(12) United States Patent
Kim et al.

(10) Patent No.: US 8,906,643 B2
(45) Date of Patent: Dec. 9, 2014

(54) METHOD FOR SCREENING DRUG CANDIDATES BY USING DOMAIN PROTEIN

(75) Inventors: Hyong-Ha Kim, Daejeon (KR); Jung-Keun Suh, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 181 days.

(21) Appl. No.: 12/300,605

(22) PCT Filed: May 23, 2006

(86) PCT No.: PCT/KR2006/001928
§ 371 (c)(1),
(2), (4) Date: Nov. 12, 2008

(87) PCT Pub. No.: WO2007/136146
PCT Pub. Date: Nov. 29, 2007

(65) Prior Publication Data
US 2011/0159478 A1    Jun. 30, 2011

(51) Int. Cl.
*C12Q 1/02* (2006.01)
*G01N 33/68* (2006.01)

(52) U.S. Cl.
CPC .................. *G01N 33/68* (2013.01); *C12Q 1/02* (2013.01); *G01N 33/6845* (2013.01); *G01N 2500/00* (2013.01)
USPC .............................. 435/29; 435/32; 435/252.3

(58) Field of Classification Search
CPC ....................................................... C12Q 1/02
USPC .......................................... 435/29, 32, 252.3
See application file for complete search history.

(56) References Cited

FOREIGN PATENT DOCUMENTS

| KR | 2003-0048974 | 6/2003 |
| KR | 2003-0095896 | 12/2003 |
| WO | 00/20574 A2 | 4/2000 |

OTHER PUBLICATIONS

Dong-Soo Han, et al., "PreSPI: A domain combination based prediction system for protein-protein interaction", *Nucleic Acids Research*, 2004, vol. 32, No. 21, pp. 6312-6320.

Peter Uetz, et al., "A comprehensive analysis of protein-protein interactions in *Saccharomyces cerevisiae*", *Nature* (www.nature.com), vol. 403, Feb. 10, 2000, pp. 623-627 and Table 2 and 3 (4 pages).

Minghua Deng, et al., "Inferring Domain-Domain Interactions From Protein-Protein Interactions", *Genome Research*, Oct. 2002, vol. 12, pp. 1540-1548.

International Search Report mailed on Feb. 16, 2007 in connection with International Application No. PCT/KR2006/001928.

Christova, P.K., et al., "A cold inducible multidomain cystatin from winter wheat inhibits growth of the snow mold fungus, *Microdochium nivale*," Planta (2006) 223: 1207-1218.

Christova, P. et al., "Wheat Multi Domain Cystatin induced during cold acclimation inhibits growth of *Typhula* Snow Mold," Japanese Plant Physiological Society Abstracts (Mar. 2006), 47th, p. 121(1aJ03(083)).

Geng, M. et al., "Fission Yeast Expression Vectors Adapted for Positive Identification of Gene Insertion and Green Fluorescent Protein Fusion," BioTechniques, 25:438-444 (Sep. 1998).

Imai, Ryozo, et al., "Antibiotic Polypeptide Inherent in Wheat Multi Donmain Cystatin," Japanese Agricultural Chemical Society Lecture Abstracts (Mar. 2006), p. 30(2A07p01).

Office Action for Japanese Patent Application No. 2009-511930, mailed May 15, 2012.

Office Action for Japanese Patent Application No. 2009-511930, issued May 27, 2011, which is counterpart to U.S. Appl. No. 12/300,605.

Okui et al., "Screening of Specific Antibodies from Human Recombinant Antibody Library using Peptide Beads", Department of Molecular. Biology, Keio Univ. School of Medicine, Department Biochemistry Setsunan Univ. (Dec. 10, 2003).

*Primary Examiner* — Tekchand Saidha
(74) *Attorney, Agent, or Firm* — Edwards Wildman Palmer LLP; Kongsik Kim; Richard B. Emmons

(57) ABSTRACT

The present invention relates to a method for screening and discovering bioactive materials using specifically selected protein domains interacting with specific intracellular proteins, and more particularly, to (1) a screening method including confirmation of changes in biological activities by introducing a specific protein domain into microorganisms or animal and plant cells and (2) a screening method including confirmation of changes in biological activities after introducing the specific protein domains into a number of microorganisms or animal and plant cells. Via this method, according to the present invention, it is possible that the selected protein domains can be used to develop novel antibiotic agents with antimicrobial activity effective on bacteria resistant to conventional antibiotics while requiring less genetic information compared with a conventional drug which targets specific genes.

6 Claims, 8 Drawing Sheets

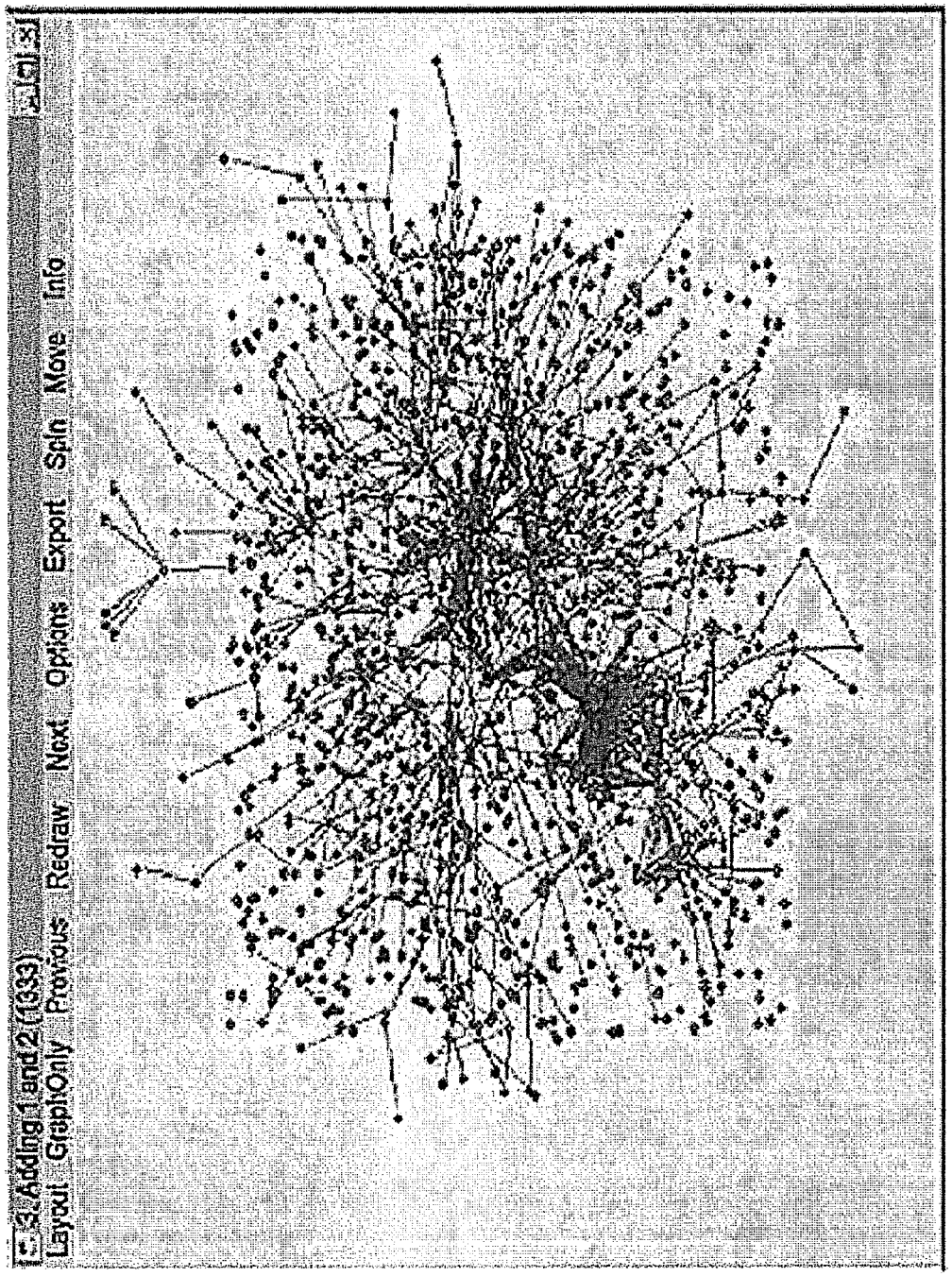

ECFP (20x20μm)

28 (20x20um)

49 (20x20um)

53 (20x20um)

18 (20×20 μm)

METHOD FOR SCREENING DRUG CANDIDATES BY USING DOMAIN PROTEIN

CROSS REFERENCE TO RELATED APPLICATIONS

This application claims the benefit under 35 U.S.C. Section 371, of International Application No. PCT/KR2006/001928, filed May 23, 2006, which claimed priority to Korean Application No. 10-2006-0045604, filed May 22, 2006 in the Korean Intellectual Property Office, the disclosures of all of which are hereby incorporated by reference.

TECHNICAL FIELD

The present invention relates to a method for screening drug candidates using protein domains interacting with specific proteins. More particularly, it relates to a method for screening to determine if specific protein domains can be utilized as drug candidates by observing changes in biological activities of microorganisms or animal and plant cells when the protein domain is introduced into microorganisms.

BACKGROUND ART

Most proteins function by interacting with other proteins or acting sequentially. The interactions between proteins play critical roles in various biological phenomena such as controlling enzymatic activities, molecule signaling, and gene expression, specificity determination of bacterial and viral infection, immune response and the like in living organisms. Therefore, it is crucial to understand interaction between proteins to clarify biological functions of novel genes and therefore discover novel drug candidates. The interaction between proteins or sequential action of proteins takes part in metabolism for survival of a living body by forming a network in an organism (FIG. 1). FIG. 1 shows a view of protein network modeling for *E. coli* or *H. pylori* [1]. The modeling method of the protein network is disclosed in Korean Patent Laid-Open Publication No. 10-2003-48974.

The interaction network between proteins existing in a living body is very complicated, even in relatively simple organisms such as bacteria. Some network factors are not critical and thus, even when they are interrupted, do not affect the viability of the organism. However, other factors existing in the center of the protein network are associated with various metabolisms and thus, when they are interrupted, the survival of the organism can be threatened [2~4]. For example, when the protein network and various metabolisms related to the growth of an organism is operated normally through normal protein interaction, i.e., between the growth hormones and the growth hormone receptors, the organism may show normal growth patterns. However, if interference within the network is present, various problems including abnormal growth patterns can be induced. Also, in case of arthritis, for example, due to excessive expression of TNF protein, the interaction between the TNF receptor and TNF activates a protein network related to inflammation response, which develops arthritis symptoms.

It is possible to predict the protein network through bioinformatics. By experimentally validating the predicted results, it is possible to identify essential proteins or essential network factors of the subject organism [5~7]. For this purpose, the biological change of an organism was observed after the protein network was blocked by mutation induction of the subject protein at gene level to knock-out the function of the protein.

Meanwhile, it is possible to identify an essential protein and its function by introducing a protein in an organism and examining the growth pattern through observation of morphological changes and cell spectroscopy [8~10].

It is known that specific sites within the protein called domains, rather than the whole protein molecule, are involved in the interaction between two or more proteins [11~14]. As shown in FIGS. 2A and 2B, for the interaction between protein A and protein B, domain a1 and domain b1 should bind. Therefore, if a protein has domain b1 which can bind to the domain a1, it can bind to protein A. In FIG. 2A is a schematic view of a specific domain for protein interaction and FIG. 2B is a schematic view of two proteins bound through domain interaction.

Conventionally, attempts were made to use a product obtained by chemically simulating an active part of an enzyme or antibody. However, many cases have shown that the simulated structures seldom performed the same function as the actual protein itself [15~17].

As a reference, RNAi (Ribonucleic acid interference) technology which is similar to this has been applied in development of new drugs [18~20]. In this technique, RNA oligomers designed to complementarily bind to a specific type of RNA molecules are introduced into an organism to nullify the function of a specific RNA. Therefore, the specific protein is not produced as a result. Based on this property, the method of removal of a protein required for pathogenic bacterial activity or possible induction of a disease is applied in treatment of the disease.

If a method for understanding the protein network and interrupting the important network factor of a microorganism or animal and plant cell system is provided, it is possible to develop bioactive substances such as novel antibiotic agents targeting a specific protein.

Accordingly, the present inventors have made efforts to develop a method for screening drug candidates and found that if a protein domain interacting with a specific protein can block the action network of the specific protein, the protein domain can be utilized as a bioactive substance such as a drug candidate. Based on this finding, the present invention has been completed.

DISCLOSURE

Technical Problem

It is an object of the present invention for a simple method for screening protein domains which disturbs, blocks or modifies protein networks of microorganisms or animal and plant cells.

Also, it is another object of the present invention to provide a method for using the above-described protein domains as novel bioactive substances for the microorganisms or animal and plant cells.

Technical Solution

In order to accomplish the above-described objects, according to the present invention, there are provided (1) screening methods to confirm (changes in) biological (physiological) activity by introducing specific protein domains into microorganisms or animal and plant cells and (2) screening methods which include confirmation of (changes in) biological activity by introducing specific protein domains into multiple microorganisms or animal and plant cells.

As shown in FIGS. 4A and 4B, when a protein b capable of binding to a protein A exists in excessive amounts, the binding of protein A and the protein domain b is predominant in a living cell and regular interactions between these proteins are affected. Consequently, the protein network is affected and thereby, the biological activity of the organism may be influenced. Based on the above reasoning, the present invention has been completed.

Now, the present invention will be described in detail.

Invention (1): Screening Method Using a Specific Protein Domain and a Specific Cell The present invention relates to a screening method validating (changes in) biological activity of a specific protein domain by introducing that specific protein domain into microorganisms or animal and plant cells, which comprises the steps of (A) selecting an essential protein from the microorganism or animal and plant cell; (B) determining a protein domain interacting with the selected essential protein; (C) introducing the determined protein domain into the microorganism or animal and plant cell; and (D) confirming change(s) in the biological activity of the microorganisms or animal and plant cells with the introduced protein domain.

The invention (1) relates to, for example, a method for screening a protein domain which shows to have a lethal effect on a specific pathogenic bacterium. Firstly, a protein expected to be essential in survival and multiplication of the specific pathogenic bacterium is selected and a protein domain expected to bind to the essential protein is introduced into the pathogenic bacterium. If the introduced protein domain binds strongly to the essential protein and disturbs the protein network in which the essential protein is involved in, reduction in multiplication or death of the pathogenic bacterium, morphological changes of the pathogenic bacterium and the like may occur.

According to the present invention, the protein may be selected using InterProScan (/), a domain database. That is, with the amino acid sequence input of a desired protein, the domain of the desired protein can be determined from the InterProScan result.

According to the present invention, the essential protein is preferably an enzyme molecule involved in cell growth, multiplication (duplication) or environmental adaptation of a specific microorganism. The essential protein can include enzymes such as helicase, deacetylase, protease, ligase and the like.

According to the present invention, in the step (C), the protein may be introduced in a form of previously prepared gene via genetic recombination. That is, the protein domain can be prepared by introducing a base sequence encoding the protein domain into a well-established recombinant protein expression system and then expressing, separating or purifying the protein domain. Here, the protein may be introduced by adding it into the culture (or cell harvest) of the microorganisms or animal and plant cells at a predetermined concentration.

According to the present invention, changes in biological activities which can be checked, may include changes in various aspects such as enzymatic activities, signal transduction, gene expression, bacterial and viral infection specificity, and immune response, etc. Some obvious changes can include changes in the multiplication rate, cell death, or morphological changes of microorganism cells.

Meanwhile, it may be possible that no changes in the bioactivities may be discovered in the step (D). Therefore, it is necessary to verify if the introduced protein domain does not have biological activity or the protein domain is not introduced into the cell properly, or is degraded after proper intracellular introduction. Therefore, it is preferable that the selected protein domain be fused with a fluorescent protein.

To accomplish this, the base sequence encoding the specific protein domain can be introduced into a well-established recombinant protein expression system fused with a fluorescent protein and the produced fusion protein is separated or purified for usage.

Examples of the fluorescent proteins which can be used in the present invention include, but are not limited to ECFP (Enhanced Cyan Fluorescent Protein), EYFP (Enhanced Yellow Fluorescent Protein), EGFP (Enhanced Green Fluorescent Protein), DsRed (*Discosoma* sp. Red Fluorescent Protein), etc.

In the step (C), the protein domain may be introduced as a form of a nucleic acid sequence encoding the protein domain introduced into an expression vector system using a microorganism or animal and plant cell. Here, it is possible to observe the change(s) in biological activities by the expression of the protein domain within the cells of microorganisms and the like.

Meanwhile, it may be possible that no changes in the bioactivities may be discovered in the step (D). Therefore, it is necessary to verify if the introduced protein domain does not have biological activity or the protein domain is not introduced into the cell properly or is degraded after proper intracellular introduction.

Therefore, it is preferable that the selected protein domain be fused with a fluorescent protein. Possible examples of fluorescent proteins for this purpose are as described above.

For example, a fusion protein composed of a fluorescent protein and a protein domain expected to interact with a specific protein can be directly introduced into *E. coli*, or a vector system having a base sequence encoding the fusion protein can be introduced into the *E. coli* cell, and the fusion protein can be expressed in *E. coli*. After a predetermined period of time, fluorescence images can be measured (Example and FIGS. 4A and 4B).

According to the present invention, the biological activities include antibiotic or antiviral activity against pathogenic bacteria, fungi and the like, anticancer activity or activity which may inhibit other diseases. That is, by the present invention, it is possible to screen new drug candidates which can be used as various antibiotic agents, antiviral agents, anticancer agents, anti-autoimmune disease agents or therapeutic agents for other diseases.

For example, when a specific protein is introduced into *E. coli*, cell growth (cell size increase) patterns may change and/or cell multiplication rate may decrease, whereas *E. coli* cells may not be able to survive when another protein domain type is introduced (Example and FIGS. 6A-6E). In these cases, the protein may act as a toxin to *E. coli*, and if the protein is shown to be nontoxic to human, it may be a novel, and effective antibiotic agent.

Invention (2) Screening Method Using Selected Protein Domain(s) and Various Cells In another aspect of the present invention, a screening method is provided for confirming if an introduced protein domain has biological activities in various microorganisms or animal and plant cells, which comprises the steps of (A) selecting an arbitrary protein domain; (B) introducing the protein domain into an arbitrary microorganisms or animal and plant cells; and (C) confirming changes in biological activities of the microorganisms or animal and plant cells by the newly introduced protein domains.

Invention (1) is a method to select protein domains showing a specific biological activity in a specific, predetermined system, whereas invention (2) is a method to screen if a predetermined, selected protein domain shows biological activity by introducing it into microorganisms or animal and plant cell systems.

In invention (2), the technical details and requirements for introduction of the protein domain in a previously prepared form, introduction of the protein domain in a fusion protein form with a fluorescent protein, or introduction of the protein domain in a form of a nucleic acid sequence fused with fluorescent protein are basically the same as described for the invention (1). Also, the details of the biological activities are as defined as above, i.e., antibiotic activity.

Advantageous Effects

As explained and proven, the present invention relates to a method for screening for a bioactive material using a protein domain interacting with a specific protein and can be effectively used in development of a bioactive material such as novel drug candidates which target new proteins, unlike the conventional methods using genes or proteins.

DESCRIPTION OF DRAWINGS

Further objects and advantages of the invention can be more fully understood from the following detailed descriptions taken in conjunction with the accompanying drawings, in which:

FIG. 1 is a view of protein network modeling using bacteria;

BEST MODE

Figure 2A:
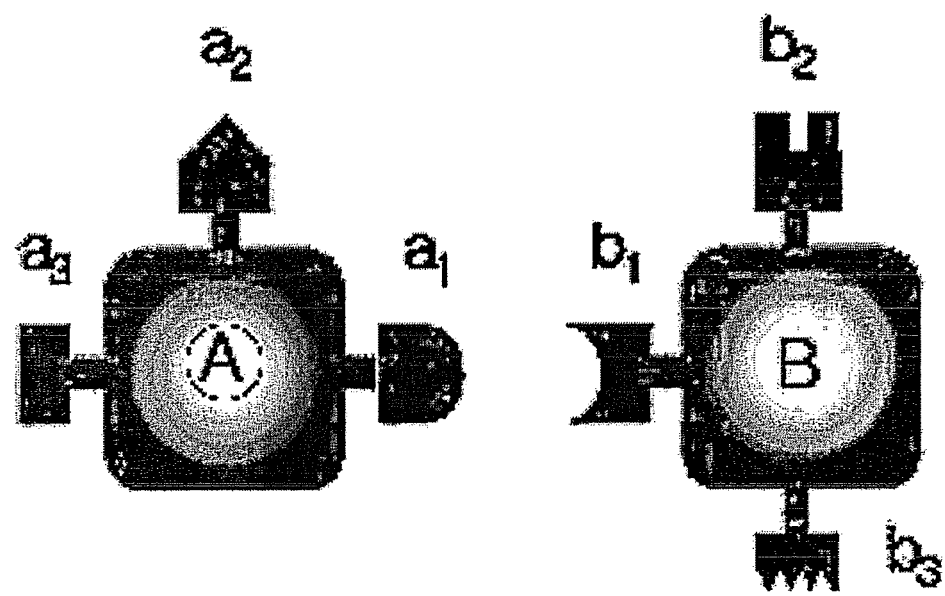
FIGS. 2A and 2B are schematic views showing the process in which a specific domain takes part in protein-protein interaction.
Figure 2B:
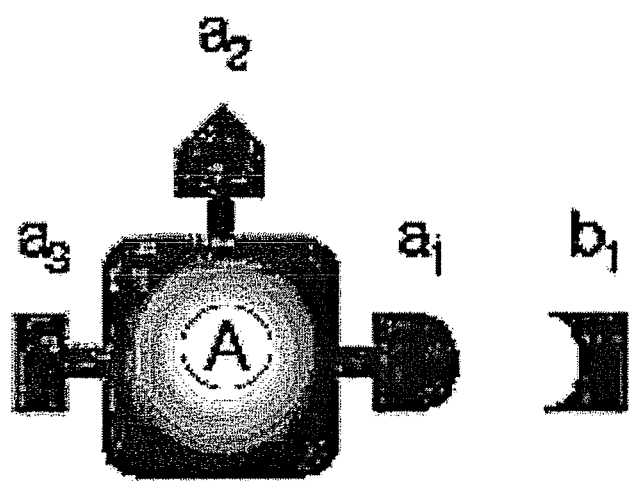
Figure 3A:
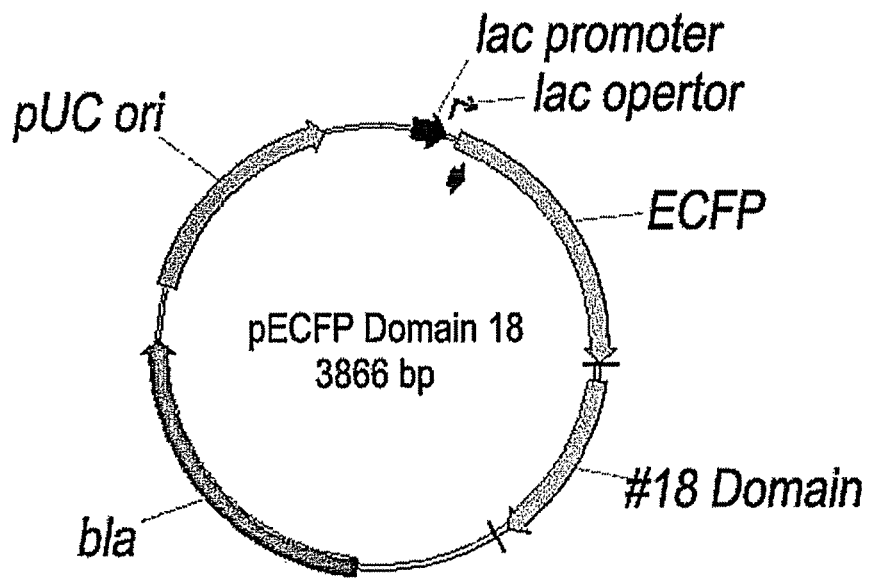
FIGS. 3A-3D are maps of the domain-pECFP fusion protein plasmid vector DNA constructed according to the present invention.
Figure 3B:
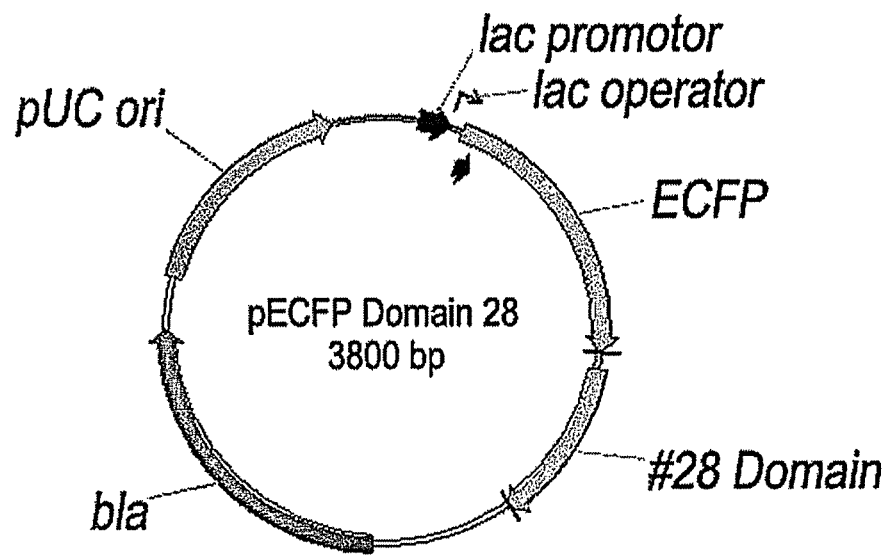
Figure 3C:
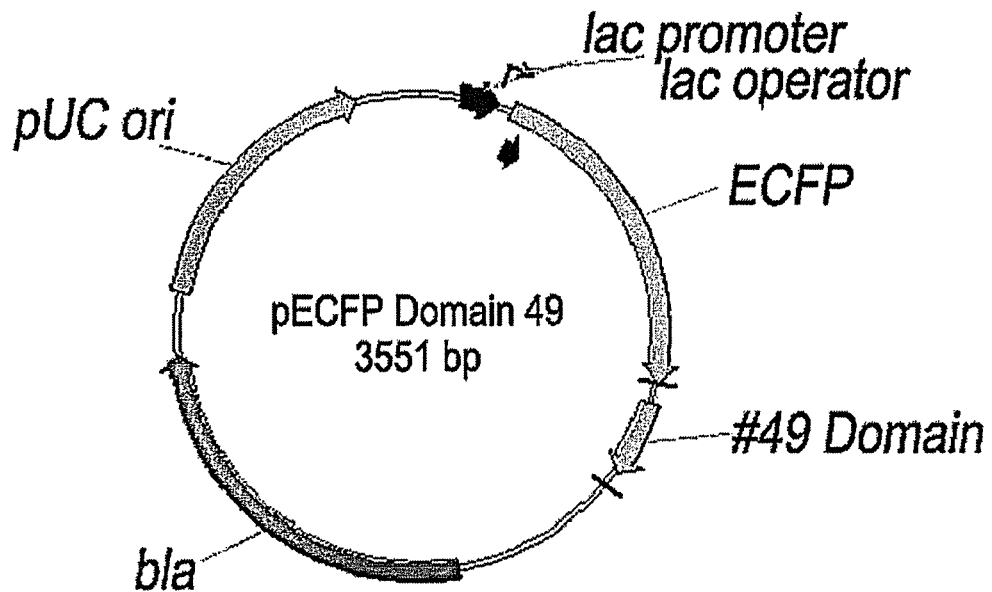
Figure 3D:
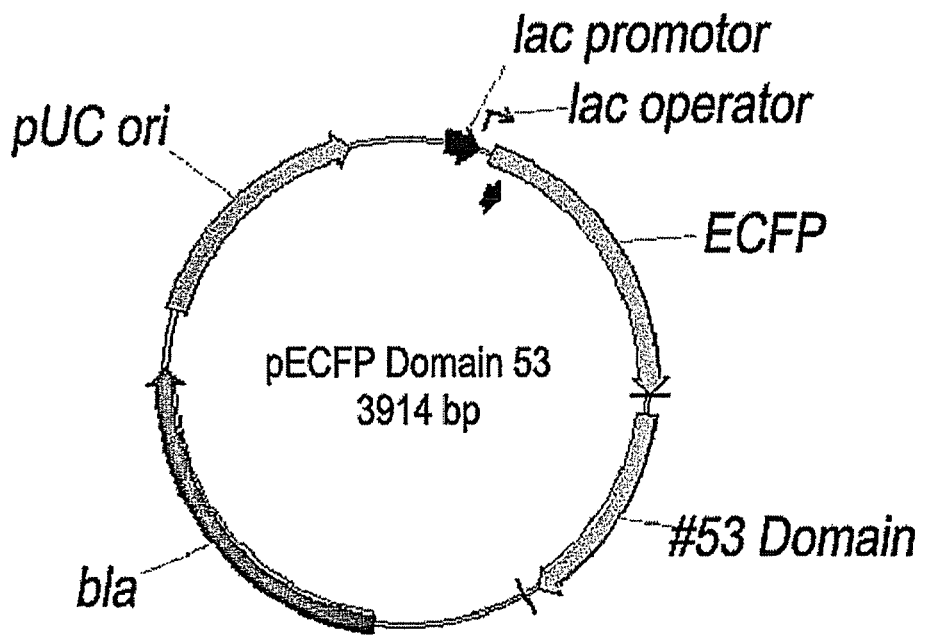
Figure 4A:
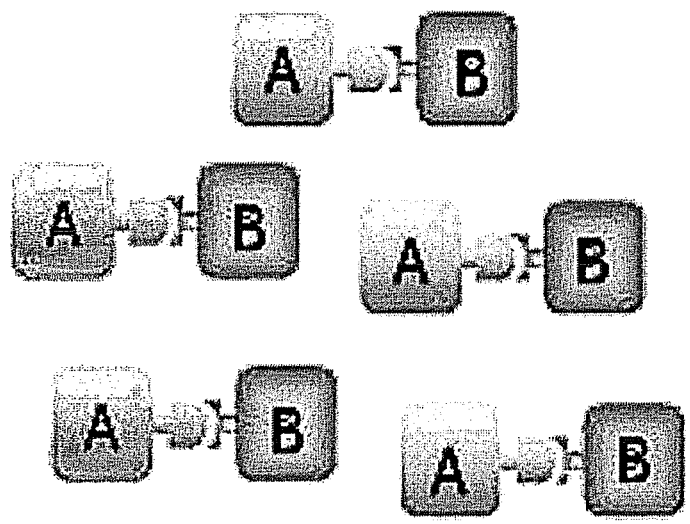
FIGS. 4A and 4B are schematic views showing blocking of the protein network via inhibition of normal protein-protein interaction.
Figure 4B:
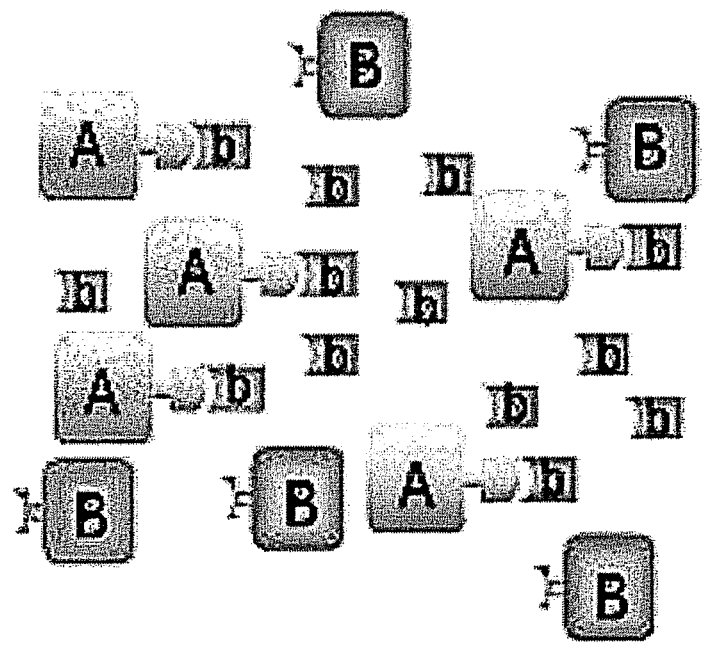

The present invention is explained in further detail using examples. The following examples are only for the illustrative purposes and the present invention is not limited thereto. In the following examples, *E. coli* is used as the material for experiment but it is clear that other microorganisms or animal and plant cells can be used under the same concept in the technical scope of the present invention. Also, as a method for introducing a protein, recombination and transformation can be employed but it is also possible to introduce protein domains by various methods including adding previously prepared protein to *E. coli* culture media (or harvest) at a predetermined concentration.

In following examples, to readily trace the introduced protein domains, protein domains are fused with fluorescent proteins.

EXAMPLES

Detecting the Changes in Biological Activities after Introducing Protein Domains A specific protein domain was introduced into bacterial cells and the effect on biological activities was examined.

(1) Selecting and Cloning a Specific Protein Domain

The selection of a specific protein domain was performed through the interproscan program (www.ebi.ac.uk/interpro), although there are many different methods for selection. The sequence of the domain part may be obtained with the amino acid sequence input of a selected protein to the program.

Several proteins of *E. coli* and *H. pylori* were selected and appropriate protein domain sequences were determined by running the program with the amino acid sequence input (Table 1).

TABLE 1

| | Protein | Origin | Domain Sequence | Domin Information | Primer Set |
|---|---|---|---|---|---|
| #18 | hypothetical protein HP 1259 | *H. pylori* | SEQ. No. 1 | Nos. 1~166 | SEQ. No. 5 SEQ. No. 6 |
| #28 | bcp (bacterioferritin comigratory protein) | *E. coli* | SEQ. No. 2 | Nos. 6~149 | SEQ. No. 7 SEQ. No. 8 |
| #49 | hypothetical protein HP 0062 | *H. pylori* | SEQ. No. 3 | Nos. 25~65 | SEQ. No. 9 SEQ. No. 10 |
| #53 | ABC transporter, ATP-binding protein | *H. pylori* | SEQ. No. 4 | Nos. 27~108 | SEQ. No. 11 SEQ. No. 12 |

Total genomic DNA of *E. coli* or *H. pylori* was used as a template and was amplified by PCR using each of the primer sets described in Table 1.

Meanwhile, fluorescent protein ECFP (Enhanced Cyan Fluorescent Protein) DNA was obtained as pECFP vector purchased from Clontech Laboratories, Inc. (Palo Alto, Calif., USA). In order to subject the pECFP vector to the TOPO reaction, Gateway Vector Conversion Reagent System was purchased; the Gateway Cassette was inserted into the pECFP vector to form a new vector pECFP-rfa. DNA which encodes the selected protein domain was amplified by PCR and the amplified DNA was confirmed by gel electrophoresis, and then subjected to the TOPO reaction and cloned into the Entry vector (pENTR-TOPO, Invitrogen Inc., Carlsbad, Calif., USA) to produce the pENTR-domain vector DNA. Each clone was examined for the presence of the insert (DNA of the protein domain) by colony PCR and the plasmid DNA was separated by DNA miniprep method, and the DNA sequence was analyzed to confirm the existence of the protein domain DNA encoding the protein domain. Only the protein domain DNA part was transferred to the pECFP-rfa vector using the confirmed pENTR-domain vector as a master clone to prepare the plasmid of the domain-pECFP fusion protein vectors. The vector DNA maps of the prepared plasmid of the domain-pECFP fusion protein vectors are shown in FIGS. 3A-3D.

The recombination reaction was performed using Gateway system (Instruction Manual of pENTR Directional TOPO Cloning Kits, Invitrogen) employing site-specific recombination features.

(2) Expression of Protein

The expression vector (pECFP-domain 28) containing the DNA of the bcp domain-ECFP fusion protein was introduced (transformed) into E. coli and the expression of the fusion protein was induced. The transformation method was performed by following the experimental manual of the Gateway System.

In order to express the bcp domain-ECFP fusion protein in E. coli, the cell line was cultured in 2 ml 2×YT medium for 16 hours at 37° C., and 0.1 ml of the culture was inoculated in 5 ml of fresh 2×YT medium, after 3 hours at 37° C., 0.05 mM IPTG was added to the cell culture and the cell culture was further incubated for an additional 2 hours to induce the expression of the fusion protein.

Other protein domains were also expressed using the same method as the bcp domain-ECFP fusion protein.

(3) Confirmation of Protein Expression by Fluorescence Measurement

If ECFP in the form fused to the protein domain is expressed in E. coli, fluorescence can be observed. Therefore, the fluorescence was measured as follows.

Firstly, transformed with the expression vector, E. coli was cultured in 5 ml of LB medium containing antibiotics (Amp 100 μg/ml, Cm 34 μg/ml) at 37° C. with 225 rpm shaking. After overnight culture, 2 ml of the culture was taken and inoculated in 10 ml of fresh LB medium. After incubation under the same conditions, when the absorbance of the cell culture has reached 0.5 to 1.0 at 600 nm, 0.05 mM IPTG was added to induce expression and E. coli cells were harvested after 3 hours.

The harvested E. coli was washed several times and suspended in 0.3 ml of PBS. 10 μl of E. coli suspension was placed on a cover glass and covered with 40 μl of low temperature gelling agarose solution (1%, w/v) for immobilization.

Figure 5:
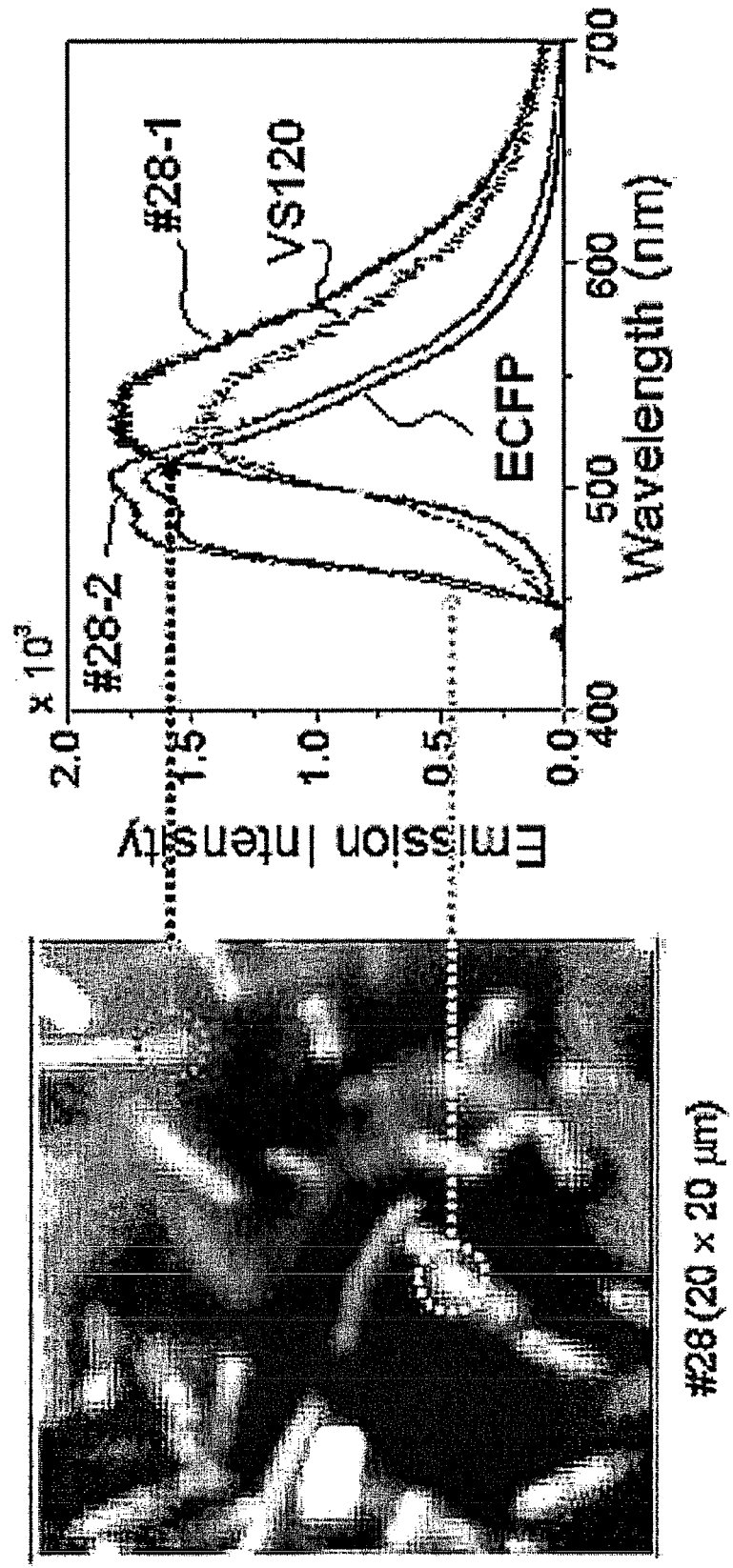
FIG. 5 and FIGS. 6A-6E are fluorescence images and fluorescence spectra showing the pattern of expression of a fusion protein composed of a protein domain and a fluorescent protein in *E. coli*.

The fluorescence image was analyzed using a confocal laser fluorescence microscope with single molecule detection sensitivity constructed by the present inventors (FIG. 5).

FIG. 5 contains a fluorescence image of bcp domain-ECFP fusion protein expressing E. coli and fluorescence spectra which represent fluorescence from parts within the single E. coli cells. A left image in FIG. 5 shows a fluorescence image of E. coli (#28) cells with bcp domain-ECFP fusion protein expressed and a right graph shows fluorescence spectra of selected intracellular regions chosen after analyzing fluorescence images of transformed bacterial cells (two E. coli cells expressing the bcp domain-ECFP fusion proteins; #28-1, #28-2), E. coli expressing ECFP only (ECFP, no bcp domain) and control E. coli (VS120), which is untransformed.

As shown in a left image in FIG. 5, the fluorescence image was bright in specific parts, suggesting that the bcp domain-ECFP fusion protein was concentrated in those specific parts. A right graph in FIG. 5 shows fluorescence spectra of the bright part and the relatively dark part of the cells. By observing these spectra, it was possible to confirm that the fluorescence was caused by the bcp domain-ECFP fusion protein which had been introduced into the cell. That is, in the spectra of the selected parts, it was noted that, as #28-2, the fluorescence spectrum of the bright portion of the cell, agreed with the fluorescence spectrum (ECFP in the graph) of ECFP which had been intentionally introduced within the cell, and the fluorescence spectrum of the relatively dark part, as #28-1, nearly agreed with the fluorescence spectrum (VS120 in the graph) of untransformed control E. coli with no new proteins introduced (no ECFP, nor bcp domain).

Therefore, it was evident that the bcp domain-ECFP fusion protein was successfully expressed in E. coli, however, was not evenly distributed throughout the transformed E. coli, whereas cells transformed to express only ECFP, the results showed otherwise. From this, it can be deduced that the intracellular localization with high fluorescence is where the specific protein and the introduced protein domain interaction exists.

(4) Changes in Biological Activities Caused by the Protein Domain Expression

In order to identify biological changes in a bacteria caused by the expression of the above described protein, the growth of the bacteria was examined (FIGS. 6A-6E).

Figure 6A:
Figure 6B:
Figure 6C:
Figure 6D:

As a result, as shown in FIGS. 6A-6D, ECFP and the bcp domain-ECFP fusion protein were expressed in E. coli. After a predetermined period of time, the growth profile of E. coli was analyzed by fluorescence imaging of the cells. In FIGS. 6B-6D, it was observed that E. coli cells with protein domains targeting interaction with the specific proteins showed different growth profiles from E. coli cells with only ECFP (no bcp domain) introduced.

Figure 7B:
FIGS. 7A-7C are images and spectra showing results obtained after introducing protein domains to *E. coli* on media plates and observing the cells.
Figure 7A:
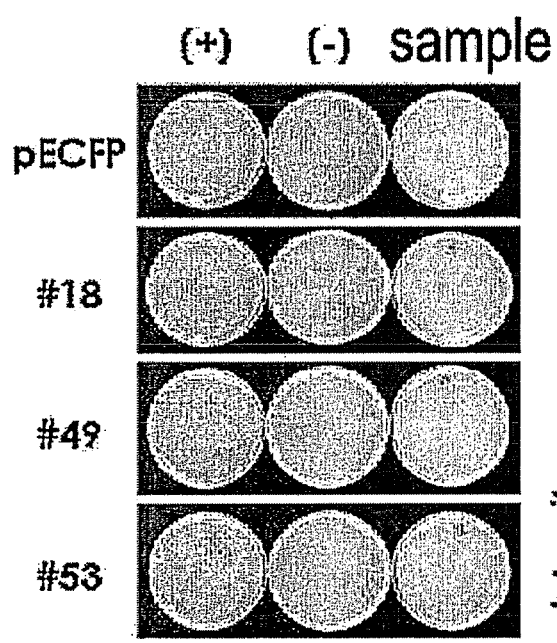
Figure 7C:
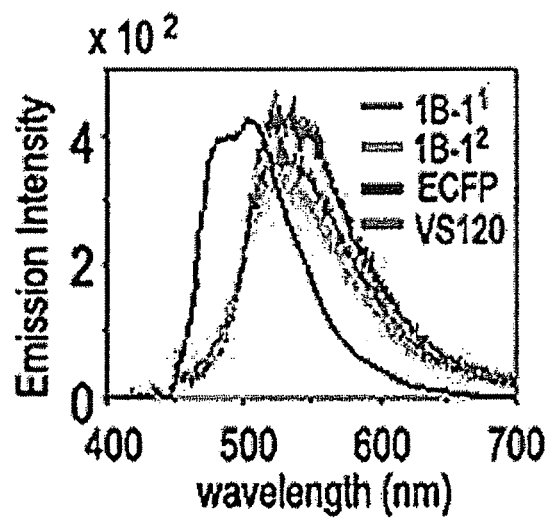

The observation results of E. coli cells grown on media plates under the above-described conditions are shown in photographs and graphs of FIGS. 7A-7C. FIG. 7B is a fluorescence image of E. coli cells showing slower growth and less cell multiplication and FIG. 7C is a fluorescence spectrum of the E. coli cells in FIG. 7B.

In drawing FIGS. 7A-7C, pECFP represents E. coli expressing only ECFP (no expressed protein domains, i.e., bcp domain, etc.), #18 represents E. coli expressing HP1259-ECFP fusion protein, #49 represents E. coli expressing HP0062-ECFP fusion protein, and #53 represents E. coli expressing HP0179-ECFP fusion protein. In FIG. 7C, 18-1$^1$ and 18-1$^2$ correspond to different colonies of #18.

Figure 6E:
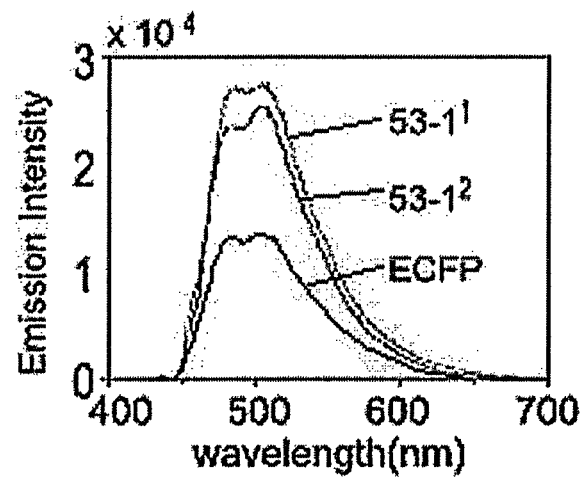

As shown in drawing FIG. 7A, in the positive control (+), approximately 100 colonies were formed whereas in the negative control (−), only 10 or less colonies were formed. In case of the samples with expressed proteins, the 'pECFP' transformants formed about 300 to 500 colonies per plate whereas samples #18, #49 and #53 formed a significantly smaller number of colonies. That is, as compared to untransformed E. coli or cells transformed only with ECFP (no additional protein domains), E. coli with introduced protein domains showed slower multiplication rate and different morphological features whereby the cells had an abnormally elongated shape, as shown in the fluorescence image. Moreover, the protein domain-ECFP fusion protein was not evenly distributed throughout the cell but was concentrated in localized intracellular regions showing relatively high concentrations of fluorescence. As shown in FIG. 6E, since the fluorescence spectrum of domain-ECFP fusion protein was detected and the spectrum was overlapping with the native ECFP spectrum in the transformed E. coli, it was confirmed that the growth pattern changes (slow growth and/or multiplication) were evident in E. coli where the protein domains were expressed.

Based on the above observation, it was confirmed that when a specific protein domain supposedly binding to an important, specific protein is introduced into E. coli and thereby interrupting (blocking) the normal protein network interaction of the specific protein, the biological activities of the target cell, such as growth (increase in cell size) and/or multiplication (increase in cell number) can be affected.

As described above, according to the present invention, an economical and rapid protein domain screening method based on detecting changes in biological activities is established.

According to the findings through Examples, when specific protein domains were introduced into *E. coli*, increase in cell size and decrease in cell multiplication rate was observed. On the other hand, there were cases of other protein domain introductions which lead to *E. coli* cell death (FIG. 5 and FIGS. 6A-6E). That is, *E. coli* cells with domain protein-ECFP fusion protein form which showed cell lethality are thought to be affected in the protein interaction network via the expressed specific protein domain blocking the network of proteins indispensable for *E. coli* survival and only the cells with very low expression level of the introduced protein domain-ECFP fusion protein could survive. Therefore, it may be possible for this protein domain to act as a controlling factor for bacterial growth including *E. coli* and thus, may be applied in developing an effective antibiotic agent with the target protein as an acting point.

These results are direct experimental evidences suggesting that via this method, a novel drug candidate targeting proteins can be developed and thus, the selected protein domains can be used to produce novel antibiotic agents with antimicrobial activity effective on bacteria resistant to conventional antibiotics.

REFERENCES

1. W. Kim, J. Park, J. K. Suh, "Large Scale Statistical Prediction of Protein-Protein Interaction by Potentially Interacting Domain (PID) pai" *Genome Informatics* 13: 42-5 (2002).
2. J. Copp, S. Wiley, M. W. Ward, P. Van der Geer, "Hypertonic shock inhibits growth factor receptor signaling, induces caspase-3 activation, and causes reversible fragmentation of the mitochondrial network" *Am. J. Physiol.* 288:C403-C415 (2005).
3. W.-K. Liu, P.-F. Yen, C.-Y. Chien, M.-J. Fann, J.-Y. Su, C.-K. Chou, "The inhibitor ABIN-2 disrupts the interaction of receptor-interacting protein with the kinase subunit IKKγ to block activation of the transcription factor NF-κB and potentiate apoptosis" *Biochem. J.* 378:867-876 (2004).
4. P. Rosa, S. Mantovani, R. Rosboch, W. B. Huttner, "Monensin and brefeldin A differentially affect the phosphorylation and sulfation of secretory proteins" *J. Biol. Chem.* 267:12227-32 (1992).
5. Q. Wang, J. He, B. Lynn, B. C. Rymond, "Interactions of the yeast SF3b splicing factor" *Mol. Cell. Biol.* 25: 10745-10754 (2005).
6. D. Hwang, J. J. Smith, D. M. Leslie, A. D. Weston, A. G. Rust, S. Ramsey, P. de Atauri, A. F. Siegel, H. Bolouri, J. D. Aitchison, L. Hood, "A data integration methodology for systems biology: Experimental verification" *Proc. Natl. Acad. Sci. USA* 102:17302-17307 (2005).
7. T. A. Wong, G. D. Fairn, P. P. Poon, M. Shmulevitz, C. R. McMaster, R. A. Singer, G. C. Johnston, "Membrane metabolism mediated by Sec14 family members influences Arf GTPase activating protein activity for transport from the trans-Golgi" *Proc. Natl. Acad. Sci. USA* 102: 12777-12782 (2005).
8. S. J. Gold, V. Zachariou, "In situ hybridization analysis of RGS mRNA regulation and behavioral phenotyping of RGS mutant mice" *Meth. Enzymol.* 389A:205-229 (2004).
9. A. Gaedigk, L. D. Bradford, K. A. Marcucci, J. S. Leeder, "Unique CYP2D6 activity distribution and genotype-phenotype discordance in black Americans" *Clin. Pharmacol. Ther.* 72:76-89 (2002).
10. E. Bakos, T. Hegedus, Z. Hollo, E. Welker, G. E. Tusnady, G. J. R. Zaman, M. J. Flens, A. Varadi, B. Sarkadi, "Membrane topology and glycosylation of the human multidrug resistance-associated protein" *J. Biol. Chem.* 271:12322-12326 (1996).
11. J. R. Giorgione, J.-H. Lin, J. A. McCammon, A. C. Newton, "Increased Membrane Affinity of the C1 Domain of Protein Kinase C.delta. Compensates for the Lack of Involvement of Its C2 Domain in Membrane Recruitment" *J. Biol. Chem.* 281:1660-1669 (2006).
12. H. Yokote, K. Fujita, X. Jing, T. Sawada, S. Liang, L. Yao, X. Yan, Y. Zhang, J. Schlessinger, K. Sakaguchi, "Transactivation of EphA4 and FGF receptors mediated by direct interactions between their cytoplasmic domains" *Proc. Natl. Acad. Sci. USA* 102:18866-18871 (2005).
13. C. Winter, A. Henschel, W. K. Kim, M. Schroeder, "SCOPPI: a structural classification of protein-protein interfaces" *Nucleic Acids Res.* 34:D310-D314 (2006).
14. B. Xie, E. Tassi, M. R. Swift, K. McDonnell, E. T. Bowden, S. Wang, Y. Ueda, Y. Tomita, A. T. Riegel, A. Wellstein, "Identification of the Fibroblast Growth Factor (FGF)-interacting Domain in a Secreted FGF-binding Protein by Phage Display" *J. Biol. Chem.* 281: 1137-1144 (2006).
15. S. Boonyarattanakalin, S. E. Martin, S. A. Dykstra, B. R. Peterson, "Synthetic Mimics of Small Mammalian Cell Surface Receptors." *J. Am. Chem. Soc.* 126:16379-16386 (2004).
16. K. Mosbach, Y. Yu, J. Andersch, L. Ye, "Generation of New Enzyme Inhibitors Using Imprinted Binding Sites: The Anti-Idiotypic Approach, a Step toward the Next Generation of Molecular Imprinting." *J. Am. Chem. Soc.* 123: 12420-12421 (2001).
17. M. L. Smythe, M. von Itzstein, "Design and Synthesis of a Biologically Active Antibody Mimic Based on an Antibody-Antigen Crystal Structure." *J. Am. Chem. Soc.* 116: 2725-33 (1994).
18. K. P. Hoeflich, D. C. Gray, M. T. Eby, J. Y. Tien, L. Wong, J. Bower, A. Gogineni, J. Zha, M. J. Cole, H. M. Stern, L. J. Murray, D. P. Davis, S. Seshagiri, "Oncogenic BRAF Is Required for Tumor Growth and Maintenance in Melanoma Models" *Cancer Res.* 66:999-1006 (2006).
19. M. Sugano, K. Tsuchida, T. Hata, N. Makino, "RNAinterference targeting SHP-1 attenuates myocardial infarction in rats" *FASEB J.* 19: 2054-2056 (2005).
20. M. Ito, K. Kawano, M. Miyagishi, K. Taira, "Genome-wide application of RNAi to the discovery of potential drug targets" *FEBS Lett.* 579:5988-5995 (2005).

INDUSTRIAL APPLICABILITY

The present invention can be used effectively in developing a bioactive material such as novel drug candidates using protein domains targeting specific proteins via predicted protein-protein interaction, which is unlike conventional methods using genes or proteins.

Particularly, the protein domains according to the present invention require less genetic information for developing a novel antibiotic agent compared with a conventional drug which targets specific genes.

The invention claimed is:

1. A method for screening protein domains for biological activity comprising the steps of:
   i. selecting a protein domain from the amino acid sequences set forth in SEQ ID NO: 1-4;
   ii. introducing said protein domain into a cell; and
   iii. measuring the growth rate, size, and morphology of said cell;

wherein a change in said cell's growth rate, size, or morphology relative to the growth profile of a control cell indicates that said protein domain exerts a biological activity.

2. The method of claim 1, wherein said protein domain is introduced into said cell using a vector encoding the nucleic acid sequence of said protein domain.

3. The method of claim 1, wherein said cell is an animal, plant, or microorganism cell.

4. The method of claim 3, wherein said microorganism is *E. coli* or *H. pylori*.

5. The method of claim 1, wherein said protein domain includes a fluorescent protein.

6. The method of claim 5, wherein said fluorescent protein is enhanced cyan fluorescent protein, enhanced yellow fluorescent protein, enhanced green fluorescent protein, or DsRed.

* * * * *

SEQUENCE LISTING

<160> NUMBER OF SEQ ID NOS: 12

<210> SEQ ID NO 1
<211> LENGTH: 205
<212> TYPE: PRT
<213> ORGANISM: Helicobacter pylori

<400> SEQUENCE: 1

```
Met Ala Cys Gly Lys Gly His Asp Ile Met Glu Val Ala Ser Pro Tyr
 1               5                  10                  15

Gly Trp Lys Lys Asn Pro Gln Lys Val Leu Asp Phe Tyr Asn Gln Arg
                20                  25                  30

Arg Arg Gln Leu Phe Glu Val Tyr Pro Asn Lys Ala His Lys Ala Leu
            35                  40                  45

Ala Glu Leu Glu Lys His Tyr Gln Val Asn Ile Ile Thr Gln Asn Val
        50                  55                  60

Asp Asp Leu His Glu Arg Ala Gly Ser Ser Arg Ile Leu His Leu His
 65                  70                  75                  80

Gly Glu Leu Leu Ser Val Arg Ser Glu Lys Asp Pro Asn Leu Val Tyr
                85                  90                  95

Arg Trp Glu Lys Asp Leu Asn Leu Gly Asp Leu Ala Lys Asp Lys Ser
            100                 105                 110

Gln Leu Arg Pro Asp Ile Val Trp Phe Gly Glu Ala Val Pro Leu Leu
        115                 120                 125

Lys Glu Ala Ile Ser Leu Val Lys Gln Ala His Leu Leu Ile Ile Ile
130                 135                 140

Gly Thr Ser Leu Gln Val Tyr Pro Ala Ala Ser Leu Tyr Thr His Ala
145                 150                 155                 160

His Lys Asp Ala Leu Ile Tyr Tyr Ile Asp Pro Lys Ala Lys Asn Ala
                165                 170                 175

His Leu Pro Gln Asn Val Gln Cys Ile Asn Glu Ser Ala Val His Ala
            180                 185                 190

Met Gln Asp Leu Met Pro Lys Leu Ile Glu Met Ala Ser
        195                 200                 205
```

<210> SEQ ID NO 2
<211> LENGTH: 156
<212> TYPE: PRT
<213> ORGANISM: Escherichia coli

<400> SEQUENCE: 2

```
Met Asn Pro Leu Lys Ala Gly Asp Ile Ala Pro Lys Phe Ser Leu Pro
 1               5                  10                  15

Asp Gln Asp Gly Glu Gln Val Asn Leu Thr Asp Phe Gln Gly Gln Arg
                20                  25                  30

Val Leu Val Tyr Phe Tyr Pro Lys Ala Met Thr Pro Gly Cys Thr Val
            35                  40                  45

Gln Ala Cys Gly Leu Arg Asp Asn Met Asp Glu Leu Lys Lys Ala Gly
        50                  55                  60

Val Asp Val Leu Gly Ile Ser Thr Asp Lys Pro Glu Lys Leu Ser Arg
 65                  70                  75                  80

Phe Ala Glu Lys Glu Leu Leu Asn Phe Thr Leu Leu Ser Asp Glu Asp
                85                  90                  95

His Gln Val Cys Glu Gln Phe Gly Val Trp Gly Glu Lys Ser Phe Met
            100                 105                 110

Gly Lys Thr Tyr Asp Gly Ile His Arg Ile Ser Phe Leu Ile Asp Ala
```

```
                    115                 120                 125
Asp Gly Lys Ile Glu His Val Phe Asp Asp Phe Lys Thr Ser Asn His
            130                 135                 140
His Asp Val Val Leu Asn Trp Leu Lys Glu His Ala
145                 150                 155

<210> SEQ ID NO 3
<211> LENGTH: 86
<212> TYPE: PRT
<213> ORGANISM: Helicobacter pylori

<400> SEQUENCE: 3

Met Ser Arg Val Gln Met Asp Thr Glu Glu Val Arg Glu Phe Val Gly
  1               5                  10                  15
His Leu Glu Arg Phe Lys Glu Leu Leu Arg Glu Val Asn Ser Leu
                 20                  25                  30
Ser Asn His Phe His Asn Leu Glu Ser Trp Arg Asp Ala Arg Arg Asp
             35                  40                  45
Lys Phe Ser Glu Val Leu Asp Asn Leu Lys Ser Thr Phe Asn Glu Phe
 50                  55                  60
Asp Glu Ala Ala Gln Glu Gln Ile Ala Trp Leu Lys Gly Arg Ile Arg
 65                  70                  75                  80
Val Leu Glu Glu Asp Tyr
                 85

<210> SEQ ID NO 4
<211> LENGTH: 213
<212> TYPE: PRT
<213> ORGANISM: Helicobacter pylori

<400> SEQUENCE: 4

Met Ile Lys Ala Ile Asn Ile Ser His Ala Phe Glu Lys Pro Leu Tyr
  1               5                  10                  15
Asn Gly Val Asn Leu His Ile Lys Pro Lys Glu Ser Leu Ala Ile Leu
                 20                  25                  30
Gly Val Ser Gly Ser Gly Lys Ser Thr Leu Leu Ser His Leu Ala Thr
             35                  40                  45
Met Leu Lys Pro Asn Ser Gly Thr Ile Ser Leu Leu Glu His Gln Asp
 50                  55                  60
Ile Tyr Ala Leu Asn Ser Lys Lys Leu Leu Glu Leu Arg Arg Leu Lys
 65                  70                  75                  80
Val Gly Ile Ile Phe Gln Ser His Tyr Leu Phe Lys Gly Phe Ser Ala
                 85                  90                  95
Leu Glu Asn Leu Gln Val Ala Ser Ile Leu Ala Lys Gln Glu Ile Asn
                100                 105                 110
His Ser Leu Leu Glu Gln Leu Gly Ile Ala His Thr Leu Lys Gln Gly
            115                 120                 125
Val Gly Glu Leu Ser Gly Gly Gln Gln Gln Arg Leu Ser Ile Ala Arg
        130                 135                 140
Val Leu Ser Lys Lys Pro Lys Ile Ile Ala Asp Glu Pro Thr Gly
145                 150                 155                 160
Asn Leu Asp Thr Thr Ser Ala Asn Gln Val Ile Ser Met Leu Gln Asn
                165                 170                 175
Tyr Ile Thr Glu Lys Glu Gly Ala Leu Val Leu Ala Thr His Asp Glu
                180                 185                 190
His Leu Ala Phe Thr Cys Ser Gln Val Tyr Arg Leu Glu Lys Glu Val
```

Leu Ile Lys Glu Lys
    210

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
caccatggct tgtggaaagg                                               20

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
cctaaatgag agcgtcttta tgc                                           23

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
caccatggcc ggtgatatcg cacc                                          24

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
ccgcggcagc acaacgtcgt ggt                                           23

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
caccctaaga gaggaagtga acagcttg                                      28

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
ccgcggatct tcctctaaaa ccctaatcc                                     29

<210> SEQ ID NO 11

```
<211> LENGTH: 24
<212> TYPE: DNA
<213> ORGANISM: Artificial Sequence
<220> FEATURE:
<223> OTHER INFORMATION: primer

<400> SEQUENCE: 11
caccgaaagc ctagcgattt tagg                                          24

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
cctaaacttc tttttctaag cgatagact                                     29
```